United States Patent
Schumacher et al.

(10) Patent No.: US 6,471,706 B1
(45) Date of Patent: Oct. 29, 2002

(54) RESORBABLE BONE DISTRACTOR AND METHOD

(75) Inventors: Brian S. Schumacher, Jacksonville, FL (US); Kevin T. Stone, Winona Lake, IN (US)

(73) Assignee: Walter Lorenz Surgical, Inc., Jacksonville, FL (US)

( * ) Notice: Subject to any disclaimer, the term of this patent is extended or adjusted under 35 U.S.C. 154(b) by 0 days.

(21) Appl. No.: 09/551,064

(22) Filed: Apr. 18, 2000

(51) Int. Cl.[7] .............................................. A61B 17/56
(52) U.S. Cl. ............................ 606/69; 606/70; 606/71
(58) Field of Search ........................ 606/69, 70, 71, 606/73, 104, 105, 61; 623/17.11, 17.15, 12.11

(56) References Cited

U.S. PATENT DOCUMENTS

| | | | | |
|---|---|---|---|---|
| 5,439,465 A | * | 8/1995 | Tumibay ..................... 606/105 |
| 5,525,646 A | * | 6/1996 | Lundgren et al. ......... 623/12.11 |
| 5,681,313 A | * | 10/1997 | Diez ............................ 606/69 |
| 5,855,580 A | * | 1/1999 | Kreidler et al. ............... 606/71 |
| 6,117,135 A | * | 9/2000 | Schlapfer ....................... 606/61 |
| 6,136,002 A | * | 10/2000 | Shih et al. ..................... 606/61 |
| 6,193,721 B1 | * | 2/2001 | Michelson .................... 606/73 |

* cited by examiner

*Primary Examiner*—Pedro Philogene
(74) *Attorney, Agent, or Firm*—Harness, Dickey & Pierce, P.L.C.

(57) ABSTRACT

A bone distractor for distracting bone on opposite sides of an osteotomy of the bone. Included are a first affixation member for affixation to the bone on one side of the osteotomy and a second affixation member for affixation to the bone on another side of the osteotomy. A distraction element includes a screw having a rotatable member engaging the first and second affixation members for distracting the first and second affixation members relative to each other in response to rotation of the rotatable member. The first and second affixation members comprise resorbable material that is resorbed in the body after distraction is complete, thereby minimizing the size of the surgical wound required to remove the non-resorbable screw. Bone screws for affixing the affixation members to bone comprise a resorbable material, whereby the bone distractor can be explanted without explanting the bone screws.

20 Claims, 4 Drawing Sheets

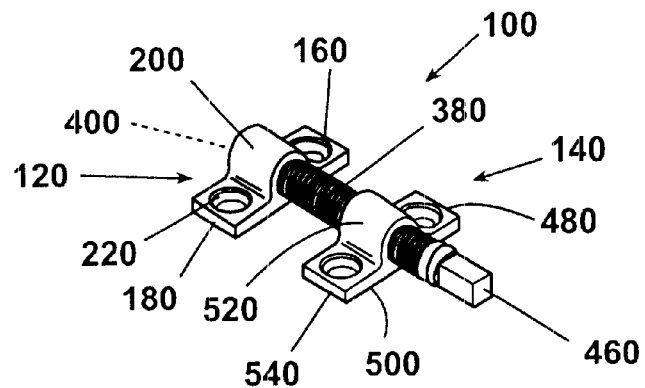
Fig. 5
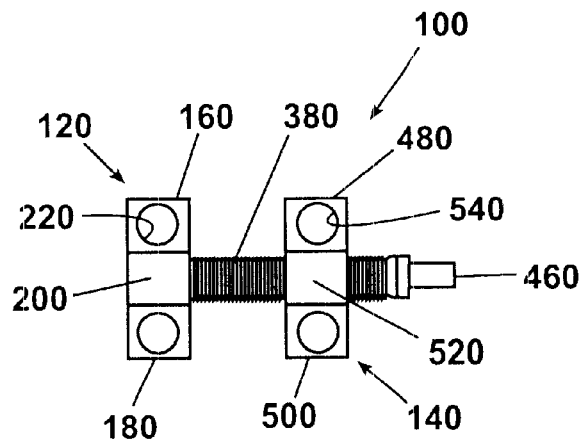
Fig. 6
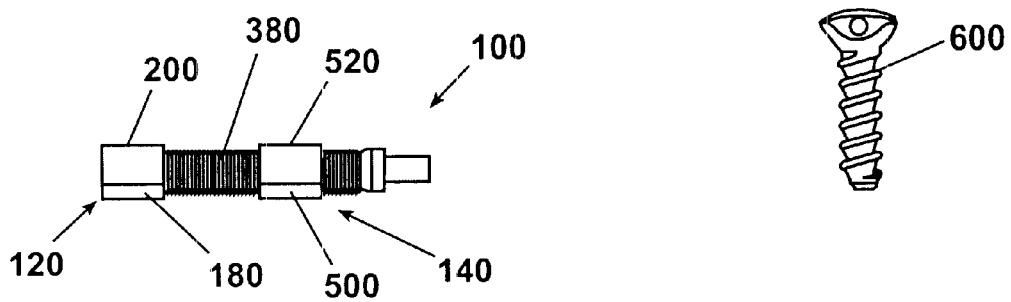
Fig. 7  Fig. 8

RESORBABLE BONE DISTRACTOR AND METHOD

BACKGROUND OF THE INVENTION

1. Field of the Invention

The present invention relates generally to apparatus for correction of craniofacial abnormalities, and more particularly to apparatus for affixation to maxillary or mandibular bones to effect distraction of the bones relative to a fracture or osteotomy.

2. Background of the Art

Various developmental disorders of the human skull result in craniofacial abnormalities in which certain bones fail to grow in proper proportion to other bones, or in which certain bones fuse prematurely, causing malformation of the midface or mandible. It is known to correct such abnormalities by separating the bones through osteotomy or fracture, and then slowly distracting the bones relative to each other, thereby inducing bone growth at the separation line. As the bones are distracted, the newly formed bone at the growth surfaces adjacent is the separation fills in the increasing gap between the bones. By this method, the midface of the cranium can be advanced forward, or the mandible can be lengthened, for example.

Apparatus for effecting distraction can involve two affixation members, in which each affixation member is temporarily affixed to the bone on opposite sides of the osteotomy, such as by bone screws, and a screw drive member that threadedly engages at least one of the affixation members. After a waiting period, or "latency period," of up to seven days following implantation, the screw drive member is rotated incrementally and periodically such that the two affixation members are driven apart at a rate of about one to two millimeters per day until the desired amount of distraction is achieved. Hence, the bones on either side of the osteotomy are distracted relative to the location of the osteotomy. Typically, after the desired amount of distraction is achieved, another waiting period, or "consolidation period," preferably at least twice the length of the period of distraction is required to allow the new bone growth to become sufficiently consolidated. Subsequently, the distraction apparatus can be removed via a new incision in the gingiva. While typical distraction rates and associated waiting periods have been discussed, it will be appreciated that faster or slower advancement of the distractor can be performed.

While the distraction apparatus is in place, the screw drive member must be accessed periodically, typically via the oral cavity, so that a driver can be engaged with the screw drive member to apply torque thereto. Such applications of torque occur over a period of time. During that period of time, the surgical wounds made during implantation of the distraction apparatus may heal substantially. After distraction is completed, it is necessary to explant the distraction apparatus, which requires significant surgery of soft tissue similar to that which occurred during implantation, thereby opening new surgical wounds in the areas of soft tissue that have already healed from the original surgical implantation. It would be advantageous to provide an improved distractor apparatus that is more easily explanted with less surgical invasion, thereby minimizing additional surgical trauma after distraction is complete and increasing the ease and speed with which the distractor apparatus can be removed. The present invention, an embodiment of which is described below with reference to the drawings, provides this and other advantages.

SUMMARY OF THE INVENTION

In accordance with one aspect of the present invention, a bone distractor is provided for distracting bone on opposite sides of an osteotomy of the bone. The bone distractor includes a first affixation member for affixation to the bone on one side of the osteotomy, and a second affixation member for affixation to the bone on another side of the osteotomy. A distraction element engages the first and second affixation members for distracting the first and second affixation members relative to each other. At least one of said first and second affixation members comprises a resorbable material.

In accordance with another aspect of the present invention, a bone distractor is provided for distracting bone on opposite sides of an osteotomy of the bone. Included are a first affixation member for affixation to the bone on one side of the osteotomy, and a second affixation member for affixation to the bone on another side of the osteotomy. A distraction element engages the first affixation member and the second affixation member for distracting the first and second affixation members relative to each other. Bone screws are provided for affixing the first and second affixation members to the bone, wherein the bone screws are constructed of a resorbable material.

In accordance with yet another aspect of the present invention, a method of distracting bone on opposite sides of an osteotomy of the bone includes the step of providing a bone distractor having a first affixation member for affixation to the bone on one side of the osteotomy, a second affixation member for affixation to the bone on another side of the osteotomy, and a distraction element engaging the first affixation member and the second affixation member for distracting the first and second affixation members relative to each other, wherein at least the first affixation member is constructed of a resorbable material. Also included is the step of providing means for affixing the first and second affixation members to bone. The step of implanting the bone distractor and affixing the first and second affixation members to bone with the means for affixing is a further step. Yet another step involves effecting distraction of the bone. Explanting the bone distractor without explanting the means for affixing is a further step.

It is an object of the present invention to provide an improved bone distractor that is readily removable after distraction is completed with minimal surgical invasion of soft tissue.

Other objects and advantages of the present invention will be apparent from the following description of a preferred embodiment, made with reference to the drawings.

BRIEF DESCRIPTION OF THE DRAWINGS

FIG. 5 is a perspective view of another embodiment of a bone distractor in accordance with the present invention.

FIG. 6 is a plan view of the bone distractor of FIG. 5.

FIG. 7 is a side view of the bone distractor of FIG. 5.

FIG. 8 is a side view of a bone screw useful in connection with the bone distractor of FIG. 5.

DETAILED DESCRIPTION OF THE PREFERRED EMBODIMENT

Figure 1:
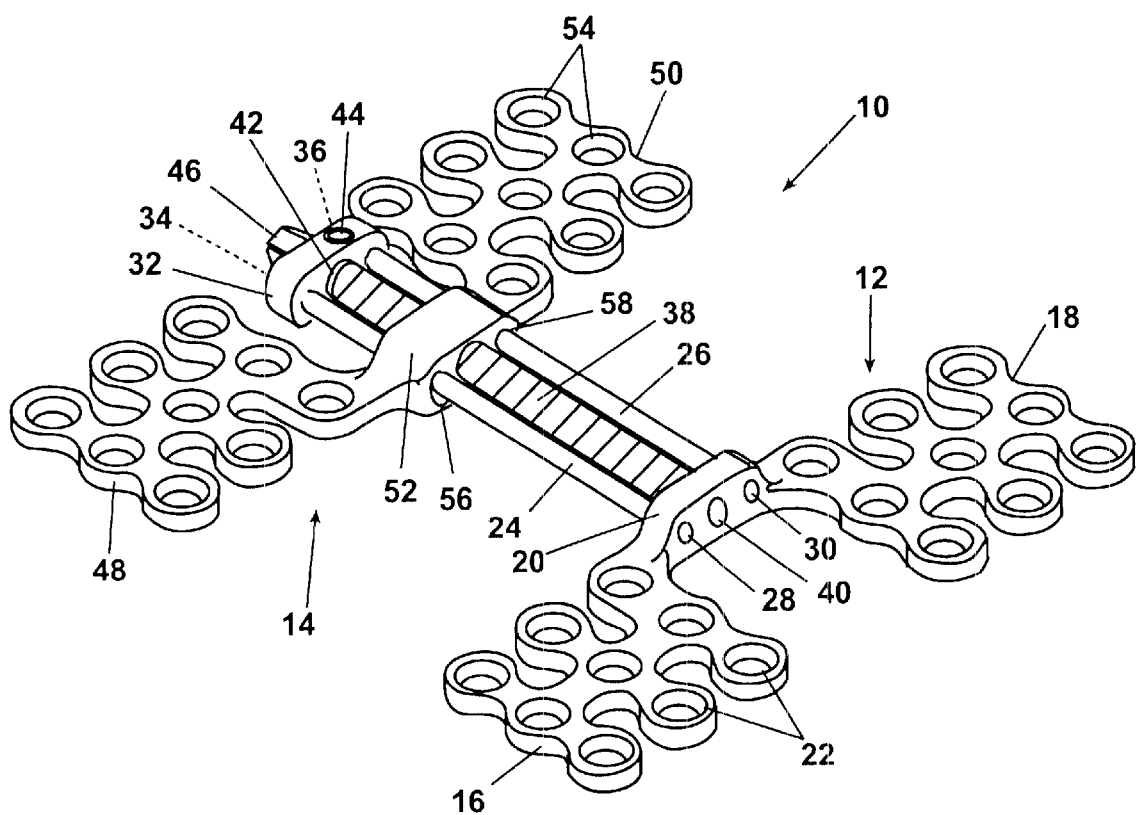
FIG. 1 is a perspective view of a bone distractor in accordance with the present invention.
Figure 2:
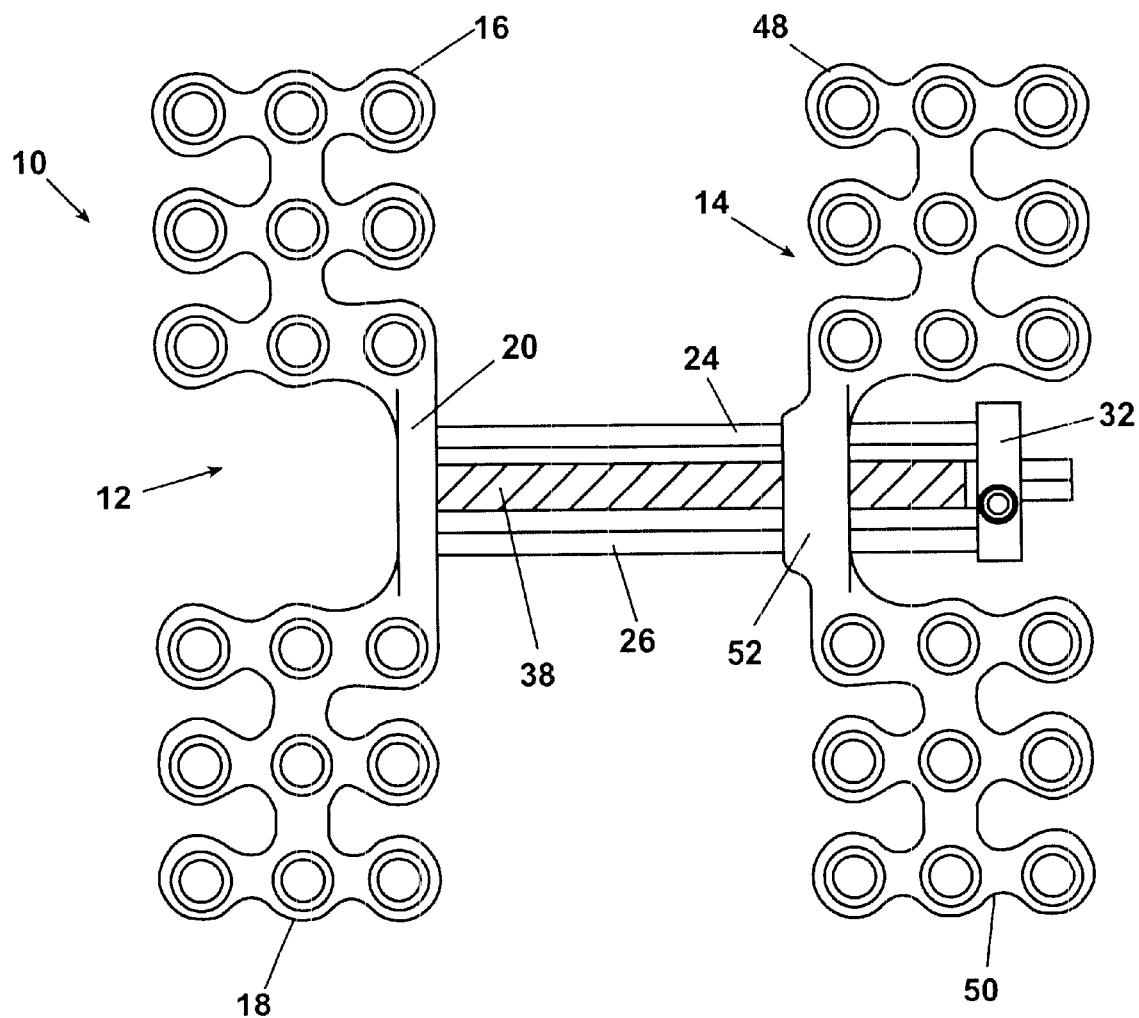
FIG. 2 is a plan view of the bone distractor of FIG. 1.
Figure 3:
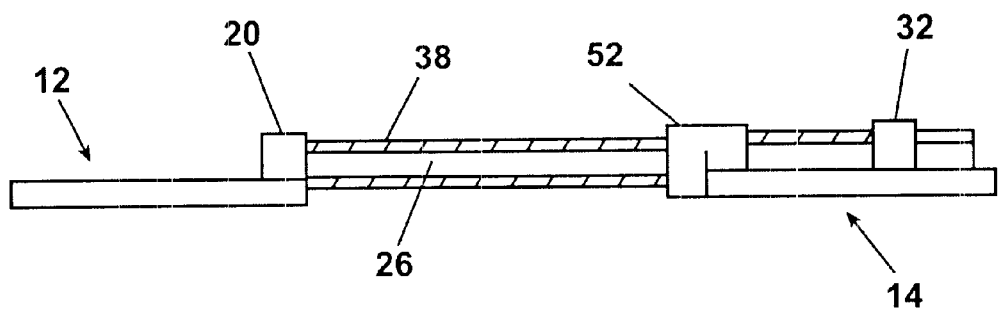
FIG. 3 is a side view of the bone distractor of FIG. 1.
Figure 4:
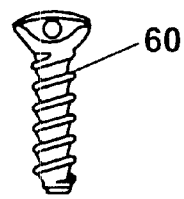
FIG. 4 is a side view of a bone screw useful in connection with the bone distractor of FIG. 1.

Referring to FIGS. 1, 2 and 3, a preferred embodiment of a bone distractor apparatus 10, constructed in accordance with the present invention, is illustrated. Bone distractor apparatus 10 includes a first affixation member 12, and a second affixation member 14 that is moveable relative to first affixation member 12.

A pair of wing elements 16 and 18 extend transversely from a central bridge portion 20 of first affixation member 12. Each wing element 16 and 18 is substantially planar and includes a plurality of screw holes 22 for receiving bone screws therethrough to secure wing elements 16 and 18 to bone, with wing elements 16 and 18 lying flat adjacent to the bone surface. Extending longitudinally, generally parallel to the plane in which wing elements 16 and 18 lie, are a pair of parallel rods 24 and 26. First ends 28 and 30 of rods 24 and 26, respectively, are friction fitted within corresponding holes in bridge portion 20 of first affixation member 12. An end member 32 has holes spaced the same as the rod holes in bridge element 20 for receiving second ends 34 and 36 of rods 24 and 26 in similar friction fit. A threaded screw rod 38 has a first non-threaded end 40 received for free rotation within a corresponding hole in bridge member 20 located between the holes 28, 30 in which rods 24 and 26 are received. Screw rod 38 has a second non-threaded portion 42 received for free rotation within a corresponding hole in end member 32 located between the holes 34, 36 in which rods 24 and 26 are received. Non-threaded portion 42 includes an annular groove disposed within the corresponding hole in end member 32. A pin 44 received through a crossbore in end member 32 lies perpendicular to screw rod 38 and engages the annular groove in non-threaded portion 42 to restrain screw rod 38 against axial movement relative to end member 32, and hence (via rods 24 and 26) against axial movement relative to bridge member 20 of first affixation member 12. A driven end 46 of screw rod 38 extends outwardly beyond end member 32. Driven end 46 has a square cross-section for engaging a driving tool.

A pair of wing elements 48 and 50 extend transversely from a central bridge portion 52 of second affixation member 14. Each wing element 48 and 50 is substantially planar and includes a plurality of screw holes 54 for receiving bone screws therethrough to secure wing elements 48 and 50 to bone, with wing elements 48 and 50 lying flat adjacent to the bone surface. Holes 56 and 58, spaced to receive rods 24 and 26 therethrough, extend longitudinally through bridge portion 52 and are sized for a free sliding relationship between second affixation member 14 and rods 24 and 26. A threaded hole 61 extends longitudinally through bridge portion 52 between holes 56 and 58, and screw rod 38 is threadedly received in threaded hole 61. In use, distraction apparatus 10 is emplaced through an incision in the gingiva with wing members 16 and 18 of first affixation member 12 on one side of an osteotomy of the mandible, for example, and wing members 48 and 50 of second affixation member 14 on the other side of the osteotomy. Each of wing members 16, 18, 48 and 50 are bent as necessary to lie flat adjacent the bone, and bone screws 60 are inserted through screw holes 22 and 54 to secure first and second affixation members 12 and 14 to respective bones on each side of the osteotomy. Distraction is effected by engaging square driven end 46 of screw rod 38 with a suitable driver tool. Torque applied to screw rod 38 causes screw rod 38 to turn, rotating freely relative to first affixation member 12 and with respect to end member 32, but in threaded engagement with second affixation member 14. Consequently, second affixation member 14 is caused to move longitudinally relative to first affixation member 12, sliding on rods 24 and 26. By rotating screw rod 38 in the appropriate direction, the respective bones to which first and second affixation members 12 and 14 are affixed are distracted relative to one another. The amount of distraction per rotation of screw rod 38 is determined by the pitch of the thread. While a threaded screw rod is employed in the disclosed embodiments to effect distraction, it is contemplated that other suitable distraction elements may be employed, including ratchet, rack and pinion, hydraulic, or gear mechanisms. In accordance with the present invention, the preferred embodiment illustrated in FIGS. 1–4 includes features that minimize the surgical trauma to soft tissue that is required for removal, or explantation, of bone distractor 10. These features include the choice of material from which certain portions of bone distractor 10 are constructed. As preferred, all elements of bone distractor 10, except screw rod 38, comprise a biologically resorbable material. The preferred resorbable material is LactoSorb® copolymer, a relatively low molecular weight copolymer that is hydrophilic and amorphous, comprising 82% L-lactic acid and 18% glycolic acid. LactoSorb® copolymer is resorbed within the body after a period of time following implantation, that period typically being about nine to fifteen months. LactoSorb® copolymer retains approximately 70% of its strength for six to eight weeks following implantation. Also, as preferred, bone screws 60 are constructed of the LactoSorb® resorbable material. Screw rod 38, as preferred, is constructed of a biologically compatible metal, such as titanium, titanium alloy, or stainless steel, capable of receiving a fine screw thread, thereby permitting small longitudinal distractions per revolution of screw rod 38. The resorbable material of the bone distractor 10 and screws 60 retain sufficient strength and integrity during the period of distraction to perform the function of firmly affixing bone distractor 10 to bone and distracting the bone portions. After distraction is complete, the resorbable portions are resorbed, or at least lose sufficient strength and integrity that the metal screw rod 38 can then be removed surgically with a minimum of trauma by being withdrawn longitudinally through a puncture type surgical wound.

In an alternative embodiment, only the bone screws are made of resorbable LactoSorb® copolymer. Resorbable screws do not need to be removed to permit removal of the distractor apparatus, thereby eliminating the multiple percutaneous surgical invasions through the cheek that would be required to align a screw drive tool with the bone screws to effect their removal. Furthermore, it is not necessary to wait for the resorbable LactoSorb® copolymer bone screws to be resorbed or lose their strength before removing the distractor apparatus. Application of heat to the LactoSorb® bone screws via a cauterizing tool will soften the bone screws sufficiently to permit the distractor apparatus to be removed. The bone screws can then be left implanted to be fully resorbed eventually.

Alternatively, to provide greater strength and distraction force, bridge portions 20 and 52 of affixation members 12 and 14 can be constructed of biologically compatible metal similar to that from which screw rod 38 is constructed, thereby providing metal-on-metal screw thread engagement. In this alternative embodiment, wing elements 16, 18, 48 and 50 are constructed of resorbable material. Rods 24 and 26, screw rod 38, cross-pin 44, as well as end member 32, can be constructed of a biologically compatible metal, if desired. These alternative embodiments require a somewhat larger surgical wound to extract the remaining metal components after resorption of the resorbable portions, but the required surgical wound is still substantially smaller than would be required if affixation member 12 and 14 were also constructed of metal, as in the prior art.

As preferred, bone screws 60 are constructed of resorbable material, thereby eliminating the need for surgical removal of the bone screws following distraction.

In an alternative embodiment, the bone distractor 10 and bone screws 60 can be constructed entirely of resorbable material, thereby eliminating the need for explantation surgery. It is preferred, however, that the drive screw be constructed of biocompatible metal for strength. The male threads of the drive screw are more easily stripped than the female threads of the bone affixation members.

Referring to FIGS. 5–7, yet another alternative embodiment is illustrated that is similar to the embodiment of FIGS. 1–4, but in which the parallel guide rods 24 and 26, as well as the end member 32, of FIGS. 1–4 are omitted. In the embodiment of FIGS. 5–7, bone distractor apparatus 100 includes a first affixation member 120, and a second affixation member 140 that is moveable relative to first affixation member 12.

A pair of wing elements 160 and 180 extend transversely from a central bridge portion 200 of first affixation member 120. Each wing element 160 and 180 is substantially planar and includes a screw hole 220 for receiving bone screws therethrough to secure wing elements 160 and 180 to bone, with wing elements 160 and 180 lying flat adjacent to the bone surface. Alternatively, wing elements 160 and 180 can be made larger and provided with a plurality of screw holes 220 through each wing element.

A pair of wing elements 480 and 500 extend transversely from a central bridge portion 520 of second affixation member 140. Each wing element 480 and 500 is substantially planar and includes a screw hole 540 for receiving bone screws therethrough to secure wing elements 480 and 500 to bone, with wing elements 480 and 500 lying flat adjacent to the bone surface.

A threaded screw rod 380 has a first non-threaded end 400 received within a corresponding hole in bridge member 200. A threaded hole extends longitudinally through bridge portion 520, and screw rod 380 is threadedly received in threaded hole. A driven end 460 of screw rod 380 extends outwardly beyond wing element 480. Driven end 460 has a square cross-section for engaging a driving tool.

Also in accordance with the present invention, the alternative embodiment illustrated in FIGS. 5–7 includes features that minimize the surgical trauma to soft tissue that is required for removal, or explantation, of bone distractor 100. As with the embodiment of FIGS. 1–4, these features include the choice of material from which certain portions of bone distractor 100 are constructed. As preferred, all elements of bone distractor 100, except screw rod 380, comprise a biologically resorbable material. The preferred resorbable material is the LactoSorb® copolymer discussed above. Also, as preferred, bone screws 600 are constructed of the LactoSorb® resorbable material. Screw rod 380, as preferred, is constructed of a biologically compatible metal, such as titanium, titanium alloy, or stainless steel, capable of receiving a fine screw thread, thereby permitting small longitudinal distractions per revolution of screw rod 380. The resorbable material of the bone distractor 100 and screws 600 retains sufficient strength and integrity during the period of distraction to perform the function of firmly affixing bone distractor 100 to bone and distracting the bone portions. After distraction is complete, the resorbable portions are resorbed, or at least lose sufficient strength and integrity that the metal screw rod 380 can then be removed surgically with a minimum of trauma by being withdrawn longitudinally through a puncture type surgical wound. Alternatively, to provide greater strength and distraction force, bridge portions 200 and 520 of affixation members 120 and 140 can be constructed of biologically compatible metal similar to that from which screw rod 380 is constructed, thereby providing metal-on-metal screw thread engagement. In this alternative embodiment, wing elements 160, 180, 480 and 500 are constructed of resorbable material. Screw rod 380 can be constructed of a biologically compatible metal, if desired. These alternative embodiments require a somewhat larger surgical wound to extract the remaining metal components after resorption of the resorbable portions, but the required surgical wound is still substantially smaller than would be required if wing elements 160, 180, 480 and 500 were also constructed of metal, as in the prior art.

As preferred, bone screws 600 are constructed of resorbable material, thereby eliminating the need for surgical removal of the bone screws following distraction.

In an alternative embodiment, the bone distractor 100 and bone screws 600 can be constructed entirely of resorbable material, thereby eliminating the need for explantation surgery. It is preferred, however, that the drive screw be constructed of biocompatible metal for strength. The male threads of the drive screw are more easily stripped than the female threads of the bone affixation members.

The preferred method of use of the invention involves implantation of a bone distractor in which at least the bone screws are constructed of resorbable material, or as more preferred, both the bone screws and the bone affixation members of the bone distractor are constructed of resorbable materials. The bone distractor is implanted via the oral cavity and through an incision in the gingiva, with the distractor secured to the bone of the mandible with the bone screws on opposing sides of an osteotomy, as in the prior art. The gingiva overlying the bone distractor is sutured and allowed to heal, with only the driver engaging portion of the drive screw protruding through the gingiva for access within the oral cavity. Either immediately following implantation or after a waiting period, or "latency period," of up to seven days, the drive screw is rotated periodically to effect distraction at a preferred rate of about one to two millimeters per day, until the desired amount of distraction is achieved. After another waiting period, or "consolidation period," preferably at least about twice as long as the period during which distraction was effected, at least a portion of the implanted bone distractor is explanted through an incision in the gingiva. If only the bone screws are resorbable, then removal of the bone distractor is significantly easier and faster than in the prior art because the bone screws need not be removed and percutaneous access to the screws through the cheek is not required, resulting in less surgical trauma to the patient. If also at least the bone affixation members of the bone distractor are constructed of resorbable material, then the incision in the gingiva through which explantation is effected is substantially smaller than that required to remove wholly non-resorbable prior art devices. If the entire bone distractor is constructed of resorbable material, then the explantation step can be eliminated.

Although the above description of a preferred embodiment is given in some detail, limitation of the invention to the described details is not intended. Other configurations and embodiments of the invention will occur to one of skill in the art and yet fall within the scope of the invention as defined in the claims appended hereto.

What is claimed is:

1. A bone distractor for distracting bone on opposite sides of an osteotomy of said bone, comprising:

a first affixation member for affixation to said bone on one side of said osteotomy;

a second affixation member for affixation to said bone on another side of said osteotomy;

a distraction element engaging said first affixation member and said second affixation member for distracting said first and second affixation members relative to each other;

wherein at least said first affixation member comprises a resorbable material.

2. The bone distractor of claim 1, in which said second affixation member comprises a resorbable material.

3. The bone distractor of claim 1, in which said resorbable material is a relatively low molecular weight copolymer that is hydrophilic and amorphous.

4. The bone distractor of claim 2, in which said resorbable material is a relatively low molecular weight copolymer that is hydrophilic and amorphous.

5. The bone distractor of claim 1, in which said distraction element includes a rotatable member.

6. The bone distractor of claim 5, in which said rotatable member comprises and elongate screw threaded rod.

7. The bone distractor of claim 6, in which said elongate screw-threaded rod comprises a biologically compatible metal.

8. The bone distractor of claim 6, in which said elongate screw-threaded rod comprises a resorbable material.

9. The bone distractor of claim 8, in which said resorbable material is a relatively low molecular weight copolymer that is hydrophilic and amorphous.

10. A bone distractor for distracting bone on opposite sides of an osteotomy of said bone, comprising:

a first affixation member for affixation to said bone on one side of said osteotomy;

a second affixation member for affixation to said bone on another side of said osteotomy;

a screw means having a rotatable member engaging said first affixation member and said second affixation member for distracting said first and second affixation members relative to each other in response to rotation of said rotatable member; and bone screws for affixing said first and second affixation members to said bone;

wherein at least said bone screws comprise a resorbable material.

11. The bone distractor of claim 10, in which at least said first affixation member comprises a resorbable material.

12. The bone distractor of claim 11, in which said second affixation member comprises a resorbable material.

13. The bone distractor of claim 11, in which said resorbable material is a relatively low molecular weight copolymer that is hydrophilic and amorphous.

14. The bone distractor of claim 12, in which said resorbable material is a relatively low molecular weight copolymer that is hydrophilic and amorphous.

15. The bone distractor of claim 10, in which said rotatable member of said screw means comprises an elongate screw-threaded rod.

16. The bone distractor of claim 15, in which said elongate screw-threaded rod comprises a biologically compatible metal.

17. The bone distractor of claim 16, in which said resorbable material is a relatively low molecular weight copolymer that is hydrophilic and amorphous.

18. A method of distracting bone on opposite sides of an osteotomy of said bone, comprising the steps of: a) providing a bone distractor having a first affixation member for affixation to said bone on one side of said osteotomy, a second affixation member for affixation to said bone on another side of said osteotomy, and a distraction element engaging said first affixation member and said second affixation member for distracting said first and second affixation members relative to each other in response to rotation of said rotatable member, wherein at least said first affixation member comprises a resorbable material; b) providing means for affixing said first and second affixation members to bone; c) implanting said bone distractor and affixing said first and second affixation members to bone with said means for affixing; d) effecting distraction of said bone; e) explanting said bone distractor without explanting said means for affixing.

19. The method of claim 18, in which said distraction element comprises a screw means having a rotatable member.

20. A method of distracting bone on opposite sides of an osteotomy of said bone, comprising the steps of: a) providing a bone distractor having a first affixation member for affixation to said bone on one side of said osteotomy, a second affixation member for affixation to said bone on another side of said osteotomy, and a screw means having a rotatable member engaging said first affixation member and said second affixation member for distracting said first and second affixation members relative to each other in response to rotation of said rotatable member; b) providing means for affixing said first and second affixation members to bone, wherein at least said means for affixing comprises a resorbable material c) implanting said bone distractor and affixing said first and second affixation members to bone with said means for affixing; d) effecting distraction of said bone; e) explanting said bone distractor without explanting said means for affixing.

* * * * *